United States Patent [19]

Kenyon et al.

[11] 3,981,775

[45] Sept. 21, 1976

[54] ENZYME INSOLUBILIZATION

[76] Inventors: Robert Sydney Kenyon, 29 Glen St., Eastwood, New South Wales, Australia, 2122; John Lyndon Garnett, 29 Arabella St., Longueville, New South Wales, Australia, 2066; Michael James Liddy, 20 Carinyan Crescent, Castle Hill, New South Wales, Australia, 2154

[22] Filed: Jan. 10, 1975

[21] Appl. No.: 540,087

[30] Foreign Application Priority Data
Jan. 18, 1974  Australia............................ 6298/74

[52] U.S. Cl.................................. 195/68; 195/63; 195/DIG. 11; 204/159.17
[51] Int. Cl.$^2$............................................ C07G 7/02
[58] Field of Search........................... 260/884, 112; 204/159.12, 159.17, 160.1, 159.15; 195/63, 68, DIG. 11

[56] References Cited

UNITED STATES PATENTS

| 3,247,133 | 4/1966 | Kwo-wei...................... 204/159.17 X |
| 3,700,609 | 10/1972 | Tregear et al. ............. 204/159.15 X |

FOREIGN PATENTS OR APPLICATIONS 801,528  9/1958  United Kingdom

*Primary Examiner*—David M. Naff
*Attorney, Agent, or Firm*—Holman & Stern

[57] ABSTRACT

Enzymes are insolubilized by attachment to a polymeric material by grafting p-nitro styrene or p-nitrophenylacrylate to the polymeric material, converting the nitro group to an amino, diazo or isothiocyanate group and covalently attaching an enzyme to the active group so formed.

11 Claims, No Drawings

ENZYME INSOLUBILIZATION

The present invention relates to a process for the insolubilization of an enzyme and more particularly a process for the insolubilization of an enzyme by the attachment of the enzyme to a graft copolymer.

Enzymes are naturally occurring catalysts which are proteinaceous in character and are normally water soluble. In recent years the desirability of using enzymes in commercial and industrial processes has achieved wider recognition due to their convenience, their specificity and their rapid action. Enzymes are relatively expensive and for economic reasons it is preferred to re-use an enzyme a number of times in a batch process, or for a prolonged period is a continuous process, and to avoid the loss of the enzyme with the product formed by the enzymatic conversion of the starting substrate. A number of workers have proposed the chemical attachment of enzymes to an insoluble carrier and such enzyme/carrier conjugates have been made. It has been found that the activity of such insolubilized enzymes is substantially lower than that of the corresponding native enzymes.

It is believed that in the known enzyme/carrier conjugates the enzyme molecules are attached to the carrier uniformly throughout the three dimensional body of the carrier; a major factor in the reduction in activity of insolubilized enzymes is due to the time required for the substrate to diffuse from the reaction solution through the carrier to reach the bound enzyme molecules and for the reaction product, or products, to diffuse back into the reaction solution.

The process according to the present invention may be carried out to produce a preponderance of bound enzyme molecules positioned on the surface of the carrier. The surface attachment of the enzyme molecules to the carrier substantially eliminates the necessity for the substrate to diffuse into the carrier and thereby avoids that cause of reduced enzyme activity. The present invention consists in a process for insolubilizing an enzyme comprising the steps of:

1. Grafting p-nitrostyrene or p-nitrophenylacrylate onto the surface of an inert polymeric carrier,
2. converting the nitro group of the grafted molecule to an amino, diazo or isothiocyanato group, and
3. covalently attaching the enzyme to the amino, diazo or isothiocyanato group to produce an enzymatically active conjugate. The invention further consists in an insoluble enzyme/carrier conjugate produced by the process according to this invention.

The inert polymeric carrier may be any suitable natural or synthetic trunk polymer to which p-nitrostyrene or p-nitrophenylacrylate can be grafted. Preferred carriers include polyvinyl chloride, polyethylene, polypropylene, polystyrene, polyacrylamide cellulose, wool and long chain carbohydrates such as starch and modified dextrose such as "Sephadex" (registered trade mark). The most preferred carrier is polyvinyl chloride dispersed in a liquid medium in which it is substantially insoluble.

The carrier may be in the form of beads, pellets, powder, plates, tubes or any other suitable configuration. If desired the polymeric carrier may itself be a shell graft polymer having a core of one polymer, e.g., polypropylene and a surface graft of a monomer such as styrene.

As is well known in the art enzymes are susceptible to both chemical and physical deactivation and the present process should be carrier out in a manner which avoids known causes of inactivity. If the use of a diazo or amino or isothiocyanato group causes inactivation of a particular enzyme, one of the other groups should be utilized for the formation of the enzyme/carrier conjugate with that particular enzyme.

The grafting of the p-nitrostyrene or p-nitrophenylacrylate to the trunk polymer is preferably induced by U.V. or ionizing radiation. The radiation may be derived from any suitable source such as an X-ray or $\gamma$-ray source, and electron beam facility or the like. Suitable conditions for the grafting of any one of the monomers to a given trunk polymer can be determined by a person skilled in the art however to following points are relevant:

1. The radiation dose is preferably given at a high dose rate and for a short time in order to maximize the surface graft as opposed to graft within the body of the carrier.
2. The solvent should preferably not swell the carrier as swelling of the carrier will increase the amount of non-surface grafting.
3. The reaction should be carried out so as to minimize homopolymerization of the monomer.
4. The reaction is preferably carried out in a solvent in which the carrier is insoluble but in which the monomer is soluble.

In a typical example a dose of from 1 to 10 MRad given at a dose rate of from 10 K Rad hr$^{-1}$ to 1 M Rad second$^{-1}$ most preferably from 50 K Rad hr$^{-1}$ to 1 M Rad minute$^{-1}$ in air the carrier being polypropylene or polyvinyl chloride powder suspended in a 1 to 40% by weight monomer solution in a suitable organic solvent such as dimethylformamide or methanol.

The nitro group of the monomer may be reduced to an amino, diazo or isothiacyanato group by any suitable reaction. If the nitro group is reduced to an amino group the enzyme may be covalently bonded to the amino group using a cross linking agent such as N,N-dicyclohexyl-carbodiimide or N-ethyl-5-phenylisoxazolium-3-sulphonate. Alternatively the amino group may be converted to a diazo or an isothiocyanato group to which the enzyme may be attached directly.

It is believed that the present reaction is specific to p-nitrostyrene and p-nitrophenylacrylate. Table 1 set out hereunder shows the specificity of the reaction in its distinction between p-nitrostyrene and m-nitrostyrene.

TABLE 1

| % Graft of Various Monomers onto Polypropylene[a] | |
|---|---|
| MONOMER | % GRAFT[b] |
| p-nitrostyrene | 5 |
| m-nitrostyrene | 0 |
| p-nitrophenylacrylate | 3 |

NOTES:
[a]Polypropylene powder (5 g) suspended in a 30% monomer solution in DMF (6 ml) and irradiated, dose 3 MRad, dose rate 200 Rad hr$^{-1}$ in air in a Cobalt 60 facility.
[b]Calculated on the basis of elemental analysis.

Table 2 set out hereunder shows the grafting of p-nitrostyrene to different trunk polymers. Samples were prepared in the normal manner using polypropylene, high density polyethylene, low density polyethylene and polyvinylchloride (PVC) as the trunk polymers.

In addition, several samples using different conditions were irradiated. These include (a) trunk polymer consisting of a polypropylene core to which styrene had been previously grafted to the extent of 10% (w/w); (b) PVC dissolved in a 50% solution of p-nitrostyrene in DMF, and (c) PVC suspended in a 30% solution of p-nitrostyrene in methanol. As PVC was soluble in DMF, the sample using methanol as solvent was prepared to compare the effects of soluble and insoluble grafting. The results are tabulated in Table 2 and indicate that under the same irradiation conditions, PVC samples gave a significantly higher graft than the other polymers. Another point of interest was that PVC grafted in the insoluble state gave twice the graft observed in the soluble state. The samples listed above were converted to the isothiocyanate derivative and coupled to trypsin (an enzyme).

TABLE 2

| Various Trunk Polymers with p-nitrostyrene[d] as monomer | |
|---|---|
| Trunk Polymer | % Graft[a] |
| Polypropylene (PP) | 5 |
| Low Density polyethylene (LDPE) | 4 |
| High Density polyethylene (HDPE) | 3 |
| Polyvinylchloride (PVC 1) | 8 |
| Polyvinylchloride[b] (PVC 2) | 13 |
| Polyvinylchloride[c] (PVC 3) | 15 |
| Poly styrene-g-polypropylene (PS) | 4 |

Notes:
[a]Calculated on the basis of elemental analysis.
[b]50% p-nitrostyrene in DMF.
[c]30% p-nitrostyrene in methanol.
[d]Trunk polymer (5 g) suspended in a 30% monomer solution in DMF(6 ml) and irradiated, dose 3MRad, dose rate 200KRad hr$^{-1}$ in air in a cobalt 60 facility.

Table 3 set out hereunder shows the activity of polymer trypsin conjugates formed by binding the enzyme trypsin to the graft copolymers of Table 2.

TABLE 3

| Analysis of Polymer-Trypsin Conjugates | |
|---|---|
| Conjugate | Esterase Activity[a] |
| PP-trypsin | Yes |
| LPDE-trypsin | Yes |
| HDPE-trypsin | Yes |
| PVC1-trypsin | Yes |
| PVC2-trypsin | Yes |
| PVC3-trypsin | Yes |
| PS-trypsin | Yes |

Notes:
[a]Spectrophotometric method using BAEE as substrate.
[b]The level of activity was found to be proportional to the amount of protein (enzyme) bound to the carrier.

Table 4 set out hereunder shows the effect of increasing the monomer concentration of the reaction medium while tables 5 and 6 show the effect of total dose on the grafting of the monomer to the polymer.

TABLE 4

| % Graft at Various Monomer Concentrations[a] | |
|---|---|
| % Monomer | % Graft[b] |
| 12.0 | 6.6 |
| 20.6 | 6.8 |
| 21.6 | 9.0 |
| 24.4 | 8.9 |
| 39.0 | 14.4 |

Notes:
[a]PVC powder (1 g) dissolved in various concentrations of p-nitrostyrene in DMF (5ml) and irradiated at 200 KRad hr$^{-1}$ in air, total dose 3 MRad, in a cobalt 60 facility.
[b]Calculated on the basis of elemental analysis.

TABLE 5

| Effect of Total Dose on Grafting to Soluble PVC[a] | |
|---|---|
| Total Dose (MRad) | % Graft[b] |
| 1 | 6.0 |
| 2 | 8.2 |
| 3 | 8.9 |
| 4 | 9.1 |

Notes:
[a]PVC (1 g) dissolved in 30% p-nitrostyrene in DMF (5 ml) and irradiated at 200 KRad hr$^{-1}$ in air in a cobalt 60 facility.
[b]Calculated on the basis of elemental composition.

TABLE 6

| Effect of Total Dose on Grafting to Insoluble PVC[a] | |
|---|---|
| Total Dose (MRad) | % Graft[b] |
| 1 | 8.3 |
| 2 | 11.7 |
| 3 | 11.9 |
| 4 | 18.8 |

Notes:
[a]PVC (1 g) suspended in 33% p-nitrostyrene in methanol (5 ml) and irradiated at 200 KRad hr$^{-1}$ in air in a cobalt 60 facility.
[b]Calculated on the basis of elemental composition.

Following is a description by way of example of method of carrying the invention into effect.

EXAMPLE 1 a. Preparation of a surface-grafted, inert-core copolymer poly (p-nitrostyrene) -g-polypropylene, by ionizing radiation initiation.

Polypropylene powder (Shell Chemical Co.) is suspended in a solution of p-nitrostyrene in N, N-dimethylformamide or methanol (30%) and the suspension irradiated by γ-radiation to a total dose of up to 10 M Rad at a dose rate of 200–400 K Rad hr$^{-1}$. Nitrostyrene monomer and homopolymer are removed by extraction of the product with a mixture of chloroform; benzene (3:1) in a soxhlet extractor for 75 hr. The extracted product is further extracted with methanol in a soxhlet extractor for 24 hr to remove chloroform and benzene. It is then dried in a vacuum oven at 70°C to remove methanol. Elemental analysis indicated a graft of 4 % by weight.

b. Reduction of poly (p-nitrostyrene) - g - polypropylene to poly (p-aminostyrene) - g - polypropylene.

Transfer the copolymer (10g) to a 500 ml 2-neck flask in about 100 ml of N, N-dimethylformamide. Heat to 100°C in an oil bath whilst stirring and add a solution of stannous chloride SnCl$_2$ 2H$_2$O (100g), in N, N-dimethylformamide (25 ml) and continue to stir for 6 hr at 100°C. Add hydrochloric acid (10M, 100 ml) and stir for a further 6 hr at 100°C. Filter the cooled reaction mixture on a sintered-glass Buchner funnel and wash the resin with N, N-dimethylformamide (6 × 50 ml) and hydrochloric acid (6N, 6 × 50 ml) alternately, then finally, with N, N-dimethylformamide (50 ml).

c. Conversion of poly (p-aminostyrene) -g- polypropylene to poly (p-isothiocyanatostyrene) -g-polypropylene.

The resin is treated with a mixture of N, N-dimethylformamide (90 ml) and triethylamine (5 ml). After stirring for 10 minutes to ensure complete neutralization, the resin is filtered and washed with N, N-dimethylformamide. The resin is then transferred to a threeneck flask (500ml) in N, N-dimethylformamide (100 ml) cool to about 4°C and, with rapid, mechanical stirring, add dropwise and simultaneously carbon disulphide (25 ml) and triethylamine (50 ml). Add sufficient N, N-dimethylformamide to the reaction mixture to nearly fill the flask, and allow it to warm to ambient temperature over a period of 4 hr, with continued rapid stirring. Again cool the flask to about 4°C, and add ethyl chloroformate (45 ml) dropwise with stirring. With slow stirring all the reaction mixture to warm to ambient temperature over a period of 12 hr. The resin is filtered and washed with chloroform until all visible triethylammonium chloride has been removed. Finally it is washed with pyridine (50 ml) and then with methanol (5 × 50 ml) and dried in a vacuum oven at 50°C.

d. Covalent bonding of trypsin (i.e., enzyme) to poly-(p-isothiocyanatostyrene) -g- Polypropylene The resin (500 mg) is suspended in bicarbonate buffer (pH 9.6, 0.1M, 10 ml) and cooled to 5°C with gentle shaking. To the suspension is added a solution of trypsin in bicarbonate buffer (10 mg/ml, 5 ml). After shaking at 5°C for 16 hr, the suspension is centrifuged and the supernatant decanted. The copolymer-trypsin conjugate is washed with water and centrifuged to remove unbound enzyme. The conjugate is then dried by lyophilization.

Tryptic activity is assayed by taking the conjugate (20 mg) and suspending it in a phosphate buffer (pH 7.6 0.1M, 1.0 ml) at 37°C. A solution of N, N-dimethylcasein (purchased from BDH Chemicals Limited, Poole, Dorset, England) in a phosphate buffer (0.05% 1.0 ml) is added and the mixture incubated for 30 min. To terminate the proteolysis, the tube containing the reaction mixture is boiled at 100°C for 20 sec. After cooling, borate buffer (pH 10.0, 0.1M 1.0 ml) is added and the mixture equilibrated at 25°C. An acqueous solution of 2,4,6-trinitrobenzenesulfonic acid (1.1M, 20 $\mu$l) is added and the mixture incubated at 25°C for 5 min. with shaking. Trinitrophenylation of free amino groups in the enzymic digest is terminated by adding a freshly prepared solution of sodium dihydrogen phosphate (0.2 M, 2.0 ml) containing sodium sulphite (0.8 mg). After centrifugation, the molar concentration of trinitrophenylated amino groups, and hence of cleaved peptide bonds, is determined spectrophotometrically at 420 nm against a blank prepared containing phosphate buffer without the addition of enzyme conjugate.

EXAMPLE 2

Preparation of surface-grafted inert-core copolymer poly (p-nitrostyrene)-g-polypropylene by U.V. irradiation Polypropylene powder (Shell Chemical Co.) is suspended in a solution of p-nitrostyrene in methanol (30%) containing benzoin ethyl ether (10%) and the suspension stirred by magnetic stirrer. The solution is then irradiated with U.V. from a Wotan W2 lamp at a distance of 10 cm from the source for 4 hours. At the end of this term the solution was worked up as in Example 1. Graft % was 11.5.

We claim:
1. A process for insolubilizing an enzyme comprising the steps of:
    1. grafting a monomer selected from the group consisting of p-nitrostyrene and p-nitrophenylacrylate onto an inert polymeric carrier using an ionizing radiation at a dose of from 1 to 10 megarads under conditions conducive to surface grafting;
    2. converting the nitro-group of the grafted polymeric carrier to an amino, diazo or isothiocyanato group; and
    3. covalently attaching the enzyme to the amino, diazo or isothiocyanato group to produce an enzymically active conjugate.
2. A process as claimed in claim 1 in which the polymeric carrier is selected from the group consisting of polyvinyl chloride polyethylene, polypropylene polystyrene, polyacrylamide, wool, and long chain carbohydrates.
3. A process as claimed in claim 1 in which the monomer is grafted to the polymeric carrier in a solvent in which the monomer is soluble and the polymeric carrier is insoluble.
4. A process as claimed in claim 1 in which the ionizing radiation is applied at a high dose rate to maximize the surface graft of the monomer to the polymeric carrier.
5. A process as claimed in claim 1 in which the ionizing radiation is applied at dose rate of from 50KRad hr$^{-1}$ to 1MRad minute$^{-1}$.
6. A process as claimed in claim 3 in which the monomer is present in the solution in an amount of from 1 to 40% by weight.
7. A process as claimed in claim 1 in which the nitro group of the grafted polymeric carrier is reduced to an amino group and is covalently bonded to the enzyme using a crosslinking agent.
8. A process as claimed in claim 8 in which the crosslinking agent is N, N-dicyclohexyl - carbodiimide or N-ethyl - 5 -phenylisoxazolium - 3 - sulphonate.
9. A process as claimed in claim 1 in which the nitro group of the grafted polymeric carrier is reduced to an amino group and is subsequently converted to a diazo or isothiocyanato group before being directly covalently bonded to the enzyme.
10. A process as claimed in claim 1 in which the enzyme is a proteolytic enzyme.
11. A process as claimed in claim 2 in which the polymeric carrier is polyvinyl chloride.

* * * * *